United States Patent [19]
Sandvig et al.

[11] Patent Number: 5,888,231
[45] Date of Patent: Mar. 30, 1999

[54] CUSTOM-MOLDED LINER FOR ARTIFICIAL LIMB SOCKET

[75] Inventors: Timothy C. Sandvig, Woodville, Wis.; Kelly T. McGurran, North Oaks; Richard E. Anderson, Vadnais Heights, both of Minn.

[73] Assignee: Minnesota Mining and Manufacturing Company, St. Paul, Minn.

[21] Appl. No.: 947,172

[22] Filed: Oct. 8, 1997

[51] Int. Cl.⁶ .......................................................... A61F 2/80
[52] U.S. Cl. .............................. 623/36; 623/901; 264/222
[58] Field of Search ...................................... 602/8, 62, 63; 623/36, 33–37; 264/222, DIG. 30; 425/2

[56] References Cited

U.S. PATENT DOCUMENTS

| | | |
|---|---|---|
| 4,376,438 | 3/1983 | Straube et al. . |
| 4,411,262 | 10/1983 | von Bonin et al. . |
| 4,433,680 | 2/1984 | Yoon . |
| 4,502,479 | 3/1985 | Garwood et al. . |
| 4,609,578 | 9/1986 | Reed . |
| 4,635,626 | 1/1987 | Lerman . |
| 4,667,661 | 5/1987 | Scholz et al. . |
| 4,683,877 | 8/1987 | Ersfeld et al. . |
| 4,832,010 | 5/1989 | Lerman . |
| 4,946,726 | 8/1990 | Sandvig et al. . |
| 5,007,937 | 4/1991 | Fishman et al. . |
| 5,163,965 | 11/1992 | Rasmusson et al. . |
| 5,184,411 | 2/1993 | Corletto . |
| 5,195,945 | 3/1993 | Sandvig et al. ............................. 602/8 |
| 5,211,667 | 5/1993 | Danforth . |
| 5,258,036 | 11/1993 | Edenbaum et al. ....................... 623/33 |
| 5,258,037 | 11/1993 | Caspers . |
| 5,314,496 | 5/1994 | Harris et al. . |
| 5,480,455 | 1/1996 | Norvell . |

FOREIGN PATENT DOCUMENTS

| | | | |
|---|---|---|---|
| 2 683 143 | 5/1993 | France . | |
| 245991 | 11/1969 | U.S.S.R. ................................... | 623/36 |

*Primary Examiner*—David H. Willse
*Attorney, Agent, or Firm*—F. Andrew Ubel

[57] ABSTRACT

A method of preparing a breathable, custom-molded liner for an artificial limb socket includes the steps of providing a liner comprising an open-celled foam material impregnated with a curable resin, activating the curable resin, and deforming the foam material by positioning a residual limb on one of opposing surfaces of the liner, and positioning the artificial limb socket on a second opposing surface of the liner until curing is substantially complete to create and retain an impression of the residual limb in the foam material. A liner blank useful for preparing an artificial limb socket, comprising a foam material impregnated with a curable resin and sewn into the shape of a sock for an artificial limb, is also described.

14 Claims, 1 Drawing Sheet

CUSTOM-MOLDED LINER FOR ARTIFICIAL LIMB SOCKET

FIELD OF THE INVENTION

This invention relates to a novel, custom-fit, breathable socket liner for an artificial limb.

BACKGROUND OF THE INVENTION

Artificial limbs are used throughout the world. Modern reinforced plastics and thermoplastics have reduced the weight of artificial limbs and improved the fit of the artificial limb socket to the residual limb. Efforts to further improve the fit between the residual limb and the artificial limb socket, and to improve the comfort of the residual limb during use, continue in the art.

Silicone socket liners are presently available and provide a custom fit between an artificial limb socket and a residual limb. The silicone socket liners, however, are not breathable. The lack of air circulation around the residual limb inside the socket leads to heat build-up and sweating, causing discomfort, skin irritation, and skin breakdown in the user.

An artificial limb socket liner that combines the features of custom-fitting, breathability, and good strength to weight ratio would provide a significant advance in the art. Such an artificial limb socket liner, and methods for preparing the same, are disclosed and claimed herein.

SUMMARY OF THE INVENTION

In general, the invention features a breathable, custom-fit liner for an artificial limb socket. The custom-fitting, breathable liner provides a highly accurate custom fit between a residual limb and an artificial limb socket, is easy to prepare, and is ready for use in a matter of hours. The socket liner includes a breathable, open-celled foam material, allowing air to circulate about the residual limb and thereby reduce heat-buildup, sweating, discomfort, and skin irritation. The use of a foam material in the liner provides for full contact between the residual limb and the liner, thereby reducing skin irritation and more uniformly distributing pressure exerted on the artificial limb socket by the residual limb.

The liner of the invention has opposing surfaces and contains a breathable, open-celled foam material impregnated with a curable resin. The liner preferably is in the form of a sock adapted to receive an artificial limb. Upon activation of the resin, the foam material, preferably having a breathable cover material adjacent thereto, may be deformed by positioning a residual limb against one opposing surface of the foam and positioning the artificial limb socket on the second opposing surface. Substantially complete curing of the resin creates and retains an impression of the residual limb and the limb socket in the foam material.

Accordingly, the invention relates, in one aspect, to a method of preparing a breathable, custom-fit liner for an artificial limb socket. The method involves the steps of providing a liner having opposing surfaces, wherein the liner includes an open-celled foam material impregnated with a curable resin; activating the curable resin; and deforming the foam material by positioning a residual limb on one of the opposing surfaces and positioning the artificial limb socket on the second of the opposing surfaces until curing is substantially complete, to create and retain an impression of the residual limb in the limb socket in the foam material.

In preferred embodiments of the invention, a breathable cover, for example an extensible fabric such as knitted fiberglass, may be provided adjacent the foam material.

The curable resin which is impregnated in the foam material preferably is an isocyanate functional prepolymer resin. The resin may be formed by reacting a polyisocyanate with a polyol, wherein the ratio of NCO groups in the polyisocyanate to OH groups in the polyol is preferably between about 2 to 1 and about 5 to 1, and more preferably between about 2.5 to 1 and about 4 to 1, and wherein the prepolymer resin has an NCO equivalent weight of about 275 to about 1000 grams of prepolymer resin per NCO group. In preferred embodiments, the prepolymer resin is formed by reacting the polyisocyanate with the polyol while those components are inside the foam material. The prepolymer resin preferably comprises between about 70% and about 95%, and more preferably between about 80% and about 90%, by weight of the foam material.

The open celled foam preferably contains from about 12 to about 48 pores per centimeters. The open celled foam preferably has a density of from about 77.5 to about 349 $Kg/m^3$.

In preferred embodiments of the invention, the artificial limb socket contains a plurality of apertures such that a composite of the socket and the cured foam liner material is breathable.

In a related aspect, the invention features a liner blank useful for preparing a breathable, custom-molded liner for an artificial limb socket. The liner blank has opposing surfaces, includes an open-celled foam material impregnated with a curable resin, and is in the form of a sock adapted to be placed over a residual limb and received in an artificial limb socket.

DETAILED DESCRIPTION OF THE INVENTION

Figure 1:
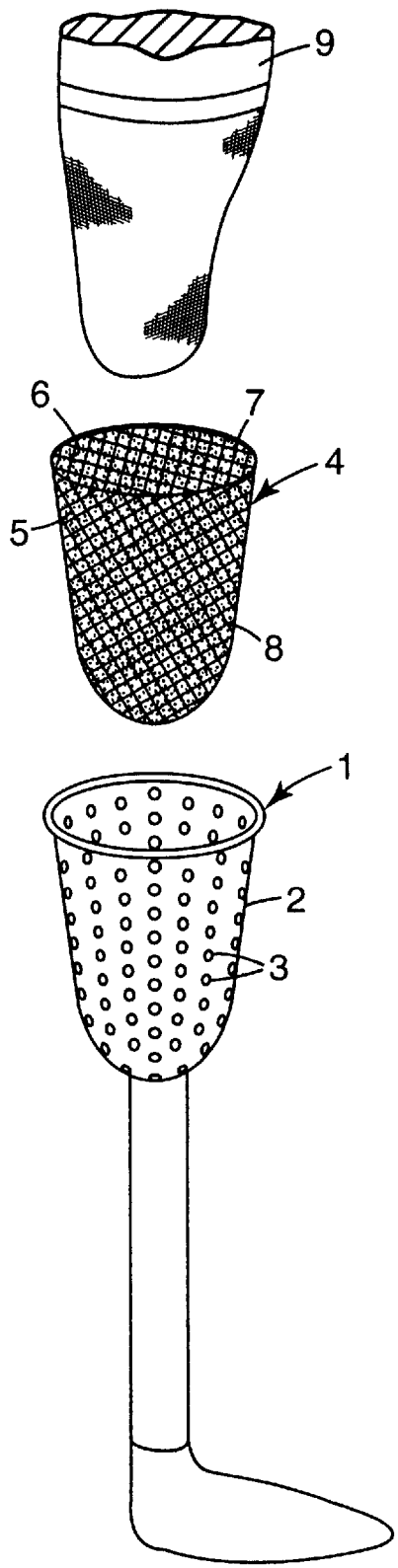
FIG. 1 is a schematic drawing illustrating the preparation of a liner for an artificial limb socket in accordance with the invention.

This invention relates to an improved liner for the socket of an artificial limb. The socket liner and method of this invention solve the problems associated with the currently used liners by providing a custom-molded, breathable socket liner, with a highly accurate fit between a residual limb and the liner, and between the liner and the socket of the artificial limb.

Accordingly, the invention features a method of preparing a breathable, custom-molded liner for an artificial limb socket. The method is useful for preparing a custom-molded socket liner for any residual limb, including above- and below-knee residual limbs of the leg as well as residual limbs of the arm.

The method first involves providing a liner for the limb socket. The liner contains an open-celled foam material impregnated with a curable resin. Typically, the liner is in the form of a sock adapted to be placed over a residual limb and adapted to be received in the artificial limb socket.

The liner preferably includes a breathable cover material adjacent the foam material. The breathable cover material may envelop the entirety of the open-celled foam material, or may cover only a portion of it, such as the portion that will be adjacent the residual limb. The breathable cover material, if present, may be selected to provide additional padding or comfort to the patient, and may also be selected to provide protection against the resin-containing foam material, before, during, or after curing. The breathable cover material may be any suitable material, including an open-celled foam layer or an extensible, breathable fabric such as a polyester or fiberglass fabric. In a preferred embodiment, the liner includes a foam material impregnated with a curable resin and an extensible fiberglass cover material bonded thereto. Suitable cover materials, including extensible fiberglass cover materials, are disclosed in U.S. Pat. No. 4,683,877, which is incorporated herein by reference. The breathable cover material should be sufficiently porous to ensure good penetration of the curing agent for the curable resin (e.g., water) into the liner, and to insure air circulation in the liner. The breathable fabric material preferably should exhibit at least 40 percent flexibility in at least one direction, as described in U.S. Pat. No. 4,683,877.

In general, the liner may be provided in any shape required for a particular application. For example, an open-celled foam sheet with a fabric cover material bonded thereto may be sewn into the form of a sock to be placed over a residual limb and into an artificial limb socket.

The open-celled foam material of the liner can comprise any one of a number of extensible foams which are open-celled, such as polyether or polyester-based polyurethane foams. Importantly, the porosity of the foam material must be such that it can be resin-loaded sufficiently to provide a satisfactory, conformed layer. In this regard, the open-celled foam preferably has from about 12 to about 48 pores/cm. As used herein, the term "pores per cm" refers to the average number of pores located along a linear centimeter of the foam sheet. The number of pores per linear centimeter may be determined, for example, by measuring the foams resistance to air flow or a pressure differential and using such information to calculate the approximate number of pores in the foam.

When the pores per cm value is decreased below 12, the foams tend to become too course or rough, and typically do not hold enough resin to provide the necessary strength for the resulting conformed layer. Foam materials having over about 39 pores per cm are not known to be presently commercially available. It will be understood, however, that the upper limit for the pores per cm parameter is limited solely by the ability to resin-load the foam sheet to the extent needed to provide sufficient strength for a conformed foam layer, while still maintaining adequate porosity. In the most presently preferred embodiment of the present invention, the open-celled foam used in the liner has at least about 18 pores per cm.

The foam material preferably has a density lower than about 349 kg/m$^3$. Foams having densities higher than about 349 kg/m$^3$ tend to preclude the resin-loading which is necessary to achieve proper strength. Preferably, the density of the foam material is between about 20 kg/m$^3$ and about 40 kg/m$^3$.

The foam preferably has an indentation force deflection (IFD) in the range of about 70 kPa to about 550 kPa, when tested as described herein. IFD is measured by compressing the center of a 40 cm×40 cm×10 cm thick foam sample (using a 10 cm diameter plunger) to a thickness of 7.5 cm (25% of its original height). More preferred foam materials have an indentation force deflection in the range of about 170 kPa to about 475 kPa, and most preferred foam materials have an indentation force deflection in the range of about 270 kpa to about 400 kPa.

The foam material preferably has a thickness of between about 0.64 cm and about 3.8 cm. After cure, the foam material may be trimmed to remove excess material.

The foam material is impregnated with a curable resin system. The presently most preferred resins for impregnating the foam sheet materials of the present invention are water curable, isocyanate functional, polyurethane prepolymers prepared by the reaction of a polyol with an excess of a polyisocyanate. The preferred resins for impregnating the foam material, and methods of preparing the same are disclosed in U.S. Pat. No. 4,946,726, which is incorporated herein by reference.

The ratio of isocyanate (NCO) groups in the polyisocyanate to hydroxyl (OH) groups in the polyol is preferably between about 2 to 1 and about 5 to 1, and more preferably between about 2.5 to 1 and about 4 to 1. The isocyanate (NCO) equivalent weight in the resultant prepolymer preferably is between about 275 to about 1000 grams of prepolymer resin per NCO group, and more preferably is between about 350 to about 700 grams of prepolymer resin per NCO group.

The breathable, custom-molded artificial limb socket liner is formed by activating the curable resin and deforming the liner between a residual limb of a patient and an artificial limb socket.

The strength and rigidity of the cured foam are dependent primarily upon the rigidity of the cured prepolymer resin rather than the initially flexible open-celled foam sheet. By maintaining the NCO:OH ratio and NCO equivalent weight within the ranges disclosed herein, safe levels of heat generated during cure are maintained, while providing a cured resin having the rigidity needed.

The resin impregnated into the foam material is intended to produce, upon curing, a "semi-rigid" foam. By "semi-rigid" it is meant that following cure, the foam will maintain some degree of resilience. Resin systems having the NCO:OH ratios and NCO equivalent weights described herein will provide cured foams having the desired levels of rigidity. A preferred mixture for impregnation into the foam material comprises the following:

| Ingredient | Source | Parts |
|---|---|---|
| Isonate 2143L | Dow Chemical U.S.A., Midland, MI | 58.38 |
| Benzoyl Chloride | Velsicol Chemical Corp., Rosemont, IL | 0.08 |
| Pluronic F-38 | BASF Corp., Mt. Olive, NJ | 5.20 |
| Polyol PPG-1025 | Union Carbide, Danbury, CT | 63.00 |
| CAB-O-SIL TS720 | Cabot Corp., Tuscola, IL | 1.30 |
| MEMPE (4-[2-{1-methyl-2-(4-morpholinyl)ethoxy}-ethyl]-morpholine) | 3M Company, St. Paul, MN (described in U.S. Pat. No. 4,705,840) | 1.30 |
| ANTIFOAM 1400 | Dow Corning, Midland, MI | 0.26 |
| IONOL (Butylated hydroxy toluene) | Sherex Chemical Co., Dublin, OH | 0.43 |
| REACTINT GREEN 960 | Milliken Chemical, Inman, SC | 0.05 |

The NCO equivalent weight of the above mixture is about 469. The NCO/OH ratio of the above mixture is about 3.18.

The polyisocyanate and polyol preferably are not reacted prior to loading the resin into the open celled foam, but rather are preferably loaded into the foam and allowed to react while within the foam sheet, to form the polyurethane prepolymer resin.

The resin system may be incorporated into the open-celled foam by layering a desired amount of resin onto or slightly beneath the surface of the foam by mechanical means, followed by rolling the coated foam piece at a predetermined roller gap which allows for complete uniform resin penetration throughout the foam.

The polyurethane prepolymer resin can be loaded into the foam material so as to comprise from about 70% to about 95%, and more preferably from about 80% to about 90%, by weight of the total article. Such a high degree of resin loading imparts to the cured foam necessary strength to function as a semi-rigid conformed layer. After loading such large percentages of resin into the foam, the resultant foam has quite good water vapor permeability and porosity thereby substantially avoiding skin maceration.

Advantageously, the resultant rigidity and strength of the cured foam material may be modified by changing the parameters of the curable resin system impregnated in the foam material. For example, a socket liner used in a residual limb for an above-knee amputee may differ in its weight bearing and strength requirements from a socket liner for a below-knee amputee. By modifying the constituents of the curable resin system, such as the NCO:OH ratio and NCO equivalent weight, the resultant cured foam material can be made more or less rigid, depending on the need for such greater or lesser rigidity and strength in a particular case.

The resin impregnated foam of the liner preferably is prepared in a relatively low humidity chamber, and the liner sealed within a water vapor impermeable package. This package is opened just prior to use. So packaged, the resin impregnated foam layer is relatively storage stable.

In a preferred embodiment of the invention, a plurality of apertures are provided in the artificial limb socket to enhance the breathability of the conformed by formed by the socket liner and artificial limb socket. A plurality of apertures in the limb socket may weaken the socket. In this circumstance, the constituents of the curable resin in the foam material can be selected to impart sufficient rigidity and strength to the composite of the liner and apertured artificial limb socket such that the artificial limb and socket/ liner provide adequate support to the residual limb during use.

The method of this invention involves activating the curable resin, positioning the residual limb against one of the opposing surfaces of the liner, and positioning the artificial limb socket against the other opposing surface of the liner. The curable resin is allowed to cure while the residual limb and socket are so positioned, to create and retain in the liner an impression of the residual limb on one opposing surface of the liner and an impression of the artificial limb socket on the other opposing surface.

After curing, additional features may be added to the custom-fit, breathable liner. For example, if a particular area of high pressure is apparent from the cured liner, additional foam may be added to that area to improve the comfort of the user.

FIG. 1 illustrates the present invention in a preferred embodiment. An artificial limb 1 includes an artificial limb socket 2. The limb socket 2 contains a plurality of apertures 3. The apertures impart breathability to the composite formed by the limb socket 2 and the liner 4. The artificial limb socket liner 4 has opposing surfaces 5 and 6, includes an open-celled foam material 7, and preferably a breathable cover material 8. The breathable cover material may be adjacent one or both of the opposing surfaces 5 and 6 of the liner 4. As discussed above, one preferred breathable cover material is an extensible knitted fiberglass material.

To prepare a custom-molded, breathable artificial limb socket liner for a residual limb, the liner 4 is wetted with water to activate the curable resin. One of the opposing surfaces 6 of the liner 4 is positioned against the residual limb 9 and the other opposing surface 5 of the liner 4 is positioned against the artificial limb. A sock may be placed over the residual limb 9 to provide comfort and protection to the residual limb during use. The activated resin is allowed to cure while the liner is positioned against the socket and residual limb. Following cure, the liner 4 is custom shaped to conform to the contours of both the artificial limb socket 2 and the residual limb 9. The shape of the residual limb 9 and socket 2 is retained in the liner. The liner 4 is breathable, and breathability of the composite of the liner 4 and limb socket 2 is enhanced by the apertures 3. When the residual limb is removed from the liner, the impression of the residual limb is retained in the liner for repeated use. The open celled foam will preferably retain resiliency such that the socket liner will remain in full contact with the residual limb during use, and will tend to uniformly distribute pressure applied to it by the residual limb.

The present invention also features a liner blank useful for preparing an artificial limb socket. The liner blank includes a foam material impregnated with a curable resin and is in the form of a sock to be fitted on an artificial limb. The liner blank may be prepared in accordance with the teachings described herein. The liner blank may be packaged and sealed in a water vapor impermeable material, and provided to health care professionals or patients for use in preparing a breathable, custom-fitting liner for an artificial limb socket.

Other embodiments of the invention are within the scope of the appended claims.

What is claimed is:

1. A method of preparing a breathable, custom-molded liner for an artificial limb socket, comprising the steps of:
   providing a liner blank having opposing surfaces, the liner comprising an open-celled foam material impregnated with a curable resin;
   activating the curable resin; and
   deforming the foam material by positioning a residual limb on one of the opposing surfaces and positioning the artificial limb socket on the second of the opposing surfaces until curing is substantially complete to create and retain an impression of the residual limb and the limb socket in the foam material, wherein the artificial limb socket comprises a plurality of apertures such that a composite comprising the socket and the cured foam material is breathable.

2. The method of claim 1, wherein the liner blank comprises an open-celled foam sheet adjacent a breathable cover material.

3. The method of claim 2, wherein the breathable cover material comprises an extensible fabric.

4. The method of claim 3, wherein the extensible fabric comprises a knitted fiberglass.

5. The method of claim 1, wherein the curable resin comprises an isocyanate functional, prepolymer resin, the prepolymer resin being formed by reacting a polyisocyanate with a polyol wherein the ratio of NCO groups in the polyisocyanate to OH groups in the polyol is between about 2 to 1 and about 5 to 1, the prepolymer resin having an NCO equivalent weight of from about 275 to about 1000 grams of prepolymer resin per NCO group.

6. The method of claim 5, wherein the ratio of NCO groups in the polyisocyanate to OH groups in the polyol is between about 2.5 to 1 and about 4 to 1.

7. The method of claim 5, wherein the prepolymer resin has an NCO equivalent weight of from about 350 to about 700 grams of prepolymer resin per NCO group.

8. The methods of claim 5, wherein the prepolymer resin is formed by reacting the polyisocyanate with the polyol while the polyisocyanate and the polyol are inside the foam material.

9. The method of claim 1, wherein the open-celled foam material contains from about 12 to about 48 pores per centimeter.

10. The method of claim 1, wherein the open-celled foam material has a density of less than about 349 kg/m$^3$.

11. The method of claim 10, wherein the open-celled foam material has a density of between about 20 kg/m$^3$ and about 40 kg/m$^3$.

12. The method of claim 5, wherein the prepolymer resin comprises between about 70% and about 95% by weight of the foam material.

13. The method of claim 12, wherein the prepolymer resin comprises from about 80% to about 90% by weight of the foam material.

14. The method of claim 1, wherein the liner blank is in the form of a sock adapted to be placed over a residual limb and adapted to be received in an artificial limb socket.

* * * * *